United States Patent [19]

Kisioka et al.

[11] Patent Number: 4,524,777
[45] Date of Patent: Jun. 25, 1985

[54] AUTOMATIC, CONTINUOUS AND INDIRECT BLOOD PRESSURE MEASUREMENT APPARATUS

[75] Inventors: Kazuya Kisioka, Tomisatomura; Kenichi Yamakoshi, Sapporo, both of Japan

[73] Assignee: Ueda Electronic Works Limited, Japan

[21] Appl. No.: 491,984

[22] Filed: May 5, 1983

[30] Foreign Application Priority Data

Feb. 25, 1983 [JP] Japan ................................. 58-30500

[51] Int. Cl.³ .............................................. A61B 5/02
[52] U.S. Cl. .................................... 128/677; 128/694
[58] Field of Search ........................ 128/677, 680–683, 128/672, 691, 694

[56] References Cited

U.S. PATENT DOCUMENTS 3,224,435 12/1965 Traite .................................... 128/682
3,920,004 11/1975 Nakayama ........................... 128/680
4,204,545 5/1980 Yamakoshi ...................... 128/680 X Primary Examiner—Lee S. Cohen
Assistant Examiner—Angela D. Sykes
Attorney, Agent, or Firm—Darby & Darby

[57] ABSTRACT

An apparatus which can measure the blood pressure automatically, continuously and indirectly, is provided. The apparatus is implemented basing upon the theory of volume compensation method and is provided with a cuff, an external force applying device, and pressure and volume sensors. The pressure of liquid contained in the cuff represents the instantaneous blood pressure under the servo control or feedback control of a volume plethysmogram. The apparatus has been improved by enabling an automatic measurement and by providing a DC level adjustment and first gain control circuit. The circuit is supplied with an output from the volume sensor, and the output is subjected to DC level adjustment and amplitude control. In addition to the above, the apparatus is automatically operated under control of a micro processor.

2 Claims, 2 Drawing Figures

AUTOMATIC, CONTINUOUS AND INDIRECT BLOOD PRESSURE MEASUREMENT APPARATUS

BACKGROUND OF THE INVENTION (a) Field of the Invention

This invention relates to an apparatus for measuring the blood pressure automatically, continuously and indirectly.

(b) Description of the Prior Art

It is known in the art that the blood pressure can be measured by applying the external pressure to an artery to be measured by an occluding cuff. This method is referred to as an auscultatory method. In this case, if the external pressure is higher than the systolic blood pressure, the bloodflow in the distal part of the cuff does not exist, and if the external pressure is kept between the systolic and diastolic blood pressure, the detection of Korotkoff sounds can be obtained by a proper transducer which is placed in the distal end of the cuff. Futhermore, if the external pressure is lower than the diastolic blood pressure, even though the bloodflow exists, its sound is not heard or is very weak. Therefore, the generally used sphygmomanometer can continuously measure only one of the systolic or diastolic blood pressures.

However, the need to measure both the systolic and diastolic blood pressures for every heart beat could not be fully satisfied, if an instrument which obtains only either one of the systolic and diastolic blood pressures, is used.

In view of the above problem, the applicant has proposed an indirectly and instantaneously measurable sphygmomanometer and filed on Mar. 23, 1979 at the U.S. Patent Office under the Ser. No. 023,267, now abandoned. This apparatus uses a volume compensation method and enables to measure continuously both the systolic and diastolic blood pressures as well as the instant blood pressure waveform. The method is based on the indirect unloading of the vascular wall, i.e., the vascular volume per unit length of blood vessel is maintained constant by applying the external pressure thereto. The applied external cuff pressure is controlled to balance, with the intravascular pressure or arterial blood pressure, so that the cuff pressure indirectly shows the arterial pressure.

The above sphygmomanometer has been found, however, not satisfactorily in that the operation and adjustment for obtaining the continuous blood pressure is done manually and it is very complicate to operate, and moreover it requires fine adjustment for each different subject or person.

SUMMARY OF THE INVENTION

It is therefore a primary object of the present invention to provide an automatic, continuous and indirect blood pressure measurement apparatus which is fully automatically operated under the control of a micro processor.

The principle upon which the present sphygmomanometer is based, is first explained. The principle is referred to in the art as a volume compensation method. In this method, the blood pressure Pb and the external cuff pressure Pc are controlled to balance with one another in order to keep the blood wall in an unloaded condition (or natural state where no external pressure is applied to the blood wall). In this condition, the external cuff pressure is used as a measure of the blood pressure. In order to carry out the measurement of the blood pressure by means of the volume compensation method, it is most important therefore to detect the unloaded condition of the blood vessel and to maintain such an unloaded condition.

It is a well known fact that the amplitude of pulsating movement of the blood vessel wall becomes maximum when average cuff and blood pressures $\overline{Pc}$ and $\overline{Pb}$ equal to each other. Since the amplitude of the blood vessel wall movement corresponds to the volume per unit length of the blood vessel (hereinafter referred to as a blood vessel volume), it is possible to detect the average cuff pressure $\overline{Pc}$, which corresponds to the average blood pressure $\overline{Pb}$, by monitoring the blood vessel volume. It is further understood that in order to maintain the unloaded condition of the blood vessel wall, first the average cuff pressure $\overline{Pc}$ ($=\overline{Pb}$) at the time of the maximum volume change is detected, and then a variable component $\Delta Pc$ is superimposed upon the average cuff pressure $\overline{Pc}$ to cancel out the blood pressure. In this unloaded condition, no external pressure is applied upon the blood vessel wall so that the blood vessel volume is held constant.

The blood vessel volume is detected by a photo sensor comprising a light emitting diode and a photo diode or transistor arranged at opposite sides of the blood vessel wall to receive light emanating from the light emitting diode. Hemoglobin contained in a red blood cell absorbs visible light to a large extent. Therefore, the amount of light received by the photo diode decreases as the volume of the blood vessel increases, thereby decreasing an output voltage of the photo diode Sv (hereinafter referred to as a volume signal) in proportion to the decrease of the cuff pressure Pc.

In summarizing the above description, the blood pressure is measured by using the volume compensation method as in the following way: First, an average cuff pressure $\overline{Pc}$ is set at a value at which the pulsating component of the volume signal Sv becomes maximum. Second, a variable pressure $\Delta Pc$ is superimposed upon the average cuff pressure $\overline{Pc}$ in such a manner that the volumetric pulse signal Sg becomes zero, i.e., the volume of the blood vessel becomes constant. The thus obtained cuff pressure Pc ($=\overline{Pc}+\Delta Pc$) represents instantaneous blood pressure at a time.

The foregoing and other objects, the features and the advantages of the present invention will be pointed out in, or apparent from, the following description of the preferred embodiment considered together with the accompanying drawings.

DETAILED DESCRIPTION OF THE PREFERRED EMBODIMENT

A preferred embodiment of the present invention will now be described with reference to the drawings.

Figure 1:
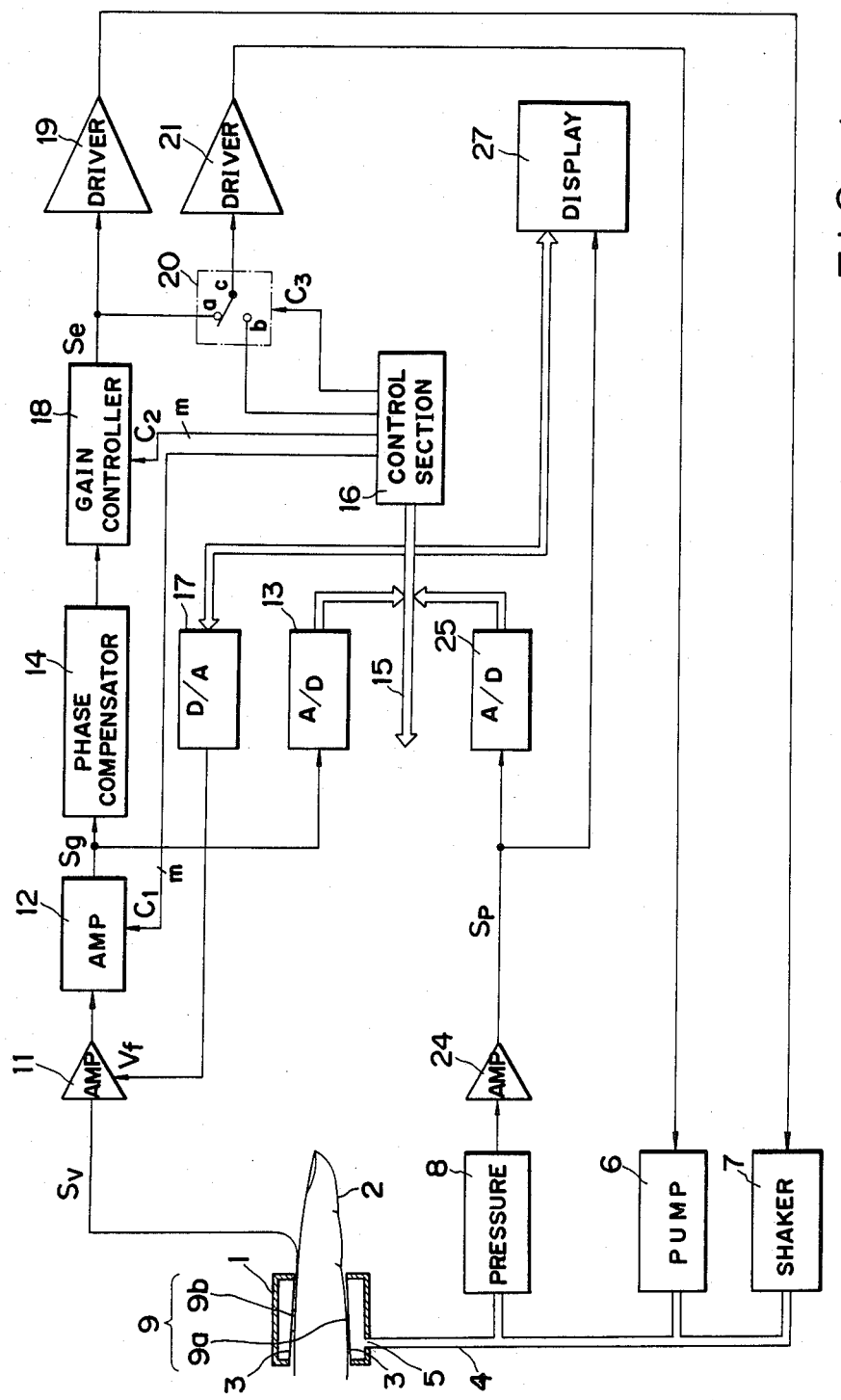
FIG. 1 is a circuit block diagram of a preferred embodiment of the automatic, continuous and indirect blood pressure measurement apparatus according to the invention.

FIG. 1 is a block diagram illustrating the construction of a preferred embodiment of the present invention. In the figure, reference number 1 denotes an annular cuff. The annular cuff 1 has a rigid outer wall and a resilient membrane 3 which is liquid-tightly sealed to an inwardly extending wall from the rigid outer wall. The space or chamber defined by the rigid outer wall, inwardly extending wall and the membrane 3 is filled with liquid, such as water 5, for imparting external pressure to the portion to be measured, such as finger 2. A linear pump 6 and shaker 7 are provided and are communicable with the chamber through a tube 4 so that the finger segment placed in the occluding cuff 1 can be compressed or decompressed by the hydraulic pressure in the chamber. The linear pump 6 generates the average cuff pressure $\overline{Pc}$ and the shaker 7 generates the variable $\Delta Pc$. In this embodiment, the linear pump 6 is driven by a geared motor which is available in commerce and is sold under the merchandise name LC-151G by Copal Electronics Company in Japan. The shaker 7 comprises a driving actuator which is sold under the merchandise name A110-50S by Hitachi Kinzoku Kabushiki Kaisha in Japan. The cuff pressure Pc ($=\overline{Pc}+\Delta Pc$) generated by the linear pump 6 and the shaker 7 compresses the artery of the finger 2 transcutaneously. A pressure sensor 8 is provided in communication with water through the tube 4 for measurement of the cuff pressure Pc. The pressure sensor 8 measures the cuff pressure and converts it into an electrical signal having a value corresponding to the cuff pressure Pc.

A volume sensor 9 is provided between the finger 2 and the membrane 3, the sensor comprising a light emitting diode 9a and a photo transistor 9b, both facing with each other through the finger 2. Light emanated from the light emitting diode 9a transmits through the finger 2 and reaches the photo transistor 9b. The amount of light transmitted is in proportion to the volume of the blood vessel concerned. Accordingly, the output voltage of the photo transistor or the volume signal Sv corresponds to the volume of the blood vessel.

The volume signal Sv is applied to a DC amplifier 11, the DC component of the output voltage being changed as desired by the application of an off-set voltage Vf. Assuming now that the DC component is 10 volts at the off-set voltage Vf=0, and that the off-set voltage is changed to 7 volts, then the resultant DC component is rendered to 8 volts. Thus, the DC amplifier 11 not only amplifies the volume signal Sv, but also eliminates the DC component from the output signal of the amplifier 11. The off-set voltage Vf is supplied from a control section 16 described later via a 12 bit digital to analog (D/A) converter 17. The output of the DC amplifier 11 is delivered to a gain control circuit 12 which is composed of a DC amplifier with a gain controlled variably. More in the concrete, the gain control circuit 12 includes a feedback circuit comprising a plurality of pairs of serially connected switch element and resistor, the pairs being connected between the output and input of the DC amplifier. The switch element is controlled to open or close depending upon a control signal C1 from the control section 16 in order that the resistance value of the feedback circuit can be varied and hence the gain can be varied as desired. The gain control circuit 12 outputs a volumetric pulse signal Sg which is an amplified signal of the output signal of the DC amplifier 11. The volumetric pulse signal Sg is then supplied to an analog to digital (A/D) converter 13 and a phase compensator 14. The 8 bit A/D converter 13 converts the volumetric pulse signal Sg into a digital signal which is transferred to the control section through a bus 15. The phase compensator 14 is supplied with a control signal (not shown) from the control section 16 and shifts the phase of the volumetric pulse signal Sg. The phase-shifted signal is then delivered to the gain control circuit 18. The gain control circuit 18 has a similar construction to the circuit 12, and generates a driver signal Se by amplifying the signal from the phase compensator 14 by the degree determined by the control signal C2 from the control section 16. This driver signal Se is supplied to a driver 19 and to an (a) terminal of a switch 20. The driver 19 comprises a linear amplifier 19 and carries out the amplification of a signal having a small DC variation. While on the other hand, a driver 21 has a hysterises characteristic and is operative only when a signal having a large DC variation is applied. The input of the driver 21 is coupled to a (c) terminal of the switch 20 which constitutes a common terminal of the switch 20. A linear pump drive signal is supplied to a (b) terminal of the switch 20. The driver signal Se and linear pump drive signal are subjected to changeover by a control signal C3 from the control section 16. The driver 19 drives the shaker 7, while the driver 21 drives the linear pump 6.

The cuff pressure Pc is detected by means of a pressure sensor 8 which generates a signal proportional to the cuff pressure Pc. The signal is amplified by an amplifier 24 which outputs a cuff pressure signal Sp. The cuff pressure signal Sp is converted into a digital signal by an A/D converter 25, and thereafter it is transferred to the control section 16 through the bus 15. The A/D converter 25 is an 8 bit arrangement. A display section 27 is also provided which operates under control of the control section 16 and displays the cuff pressure signal Sp under an appropriate scale.

The control section 16 is preferably made of a central processor unit Z80, parallel input and output Z80-PIO, read-only memory and random access memory all available from Zilog, Inc., in the U.S.A.

Figure 2:
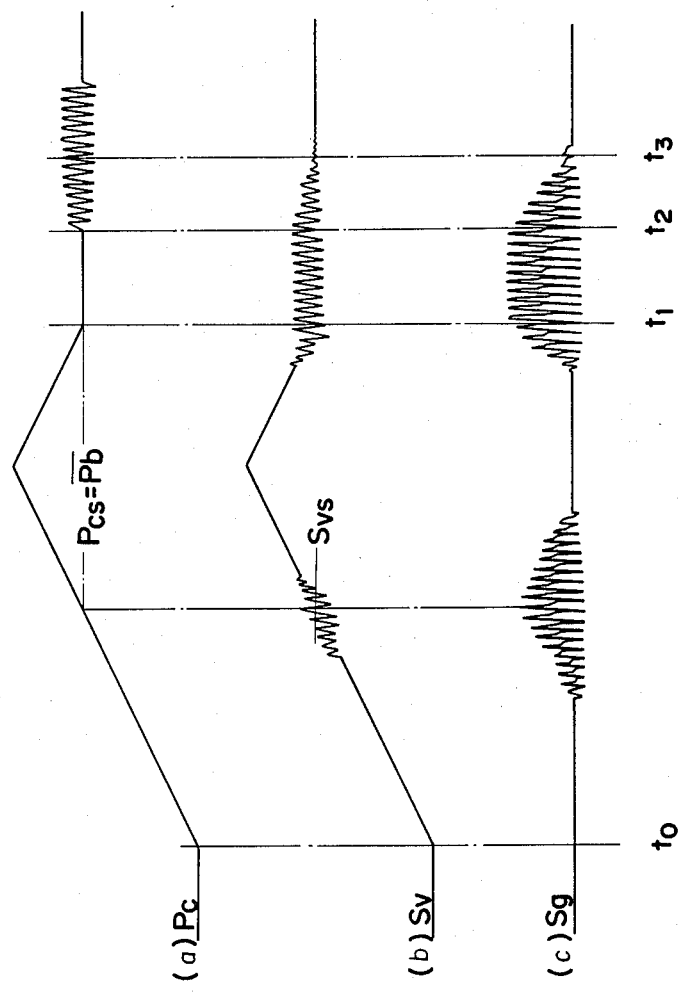
FIG. 2 shows typical waveforms of cuff pressure, volume signal and volumetric pulse signal, for illustrating the operation of the circuit shown in FIG. 1.

The operation of the automatic, continuous and indirect sphygmomanometer thus constructed will be described with reference to FIGS. 1 and 2. A finger 2 is inserted into the cuff 1 as shown in FIG. 1. A start button (not shown) is depressed to start the operation of the control section 16 at the timing to as shown in FIG. 2. The control section 16 delivers a control signal C3 to make the common terminal (c) get contact with the (b) terminal. The driver 21 is supplied with logical "1" signals as a linear pump drive signal. Accordingly, the driver 21 drives the linear pump 6 in such a manner that the cuff pressure Pc is linearly increased as shown in FIG. 2 at line (a). In compliance with the increase of the cuff pressure Pc, the volume signal Sv rises up gradually as shown at line (b). When the cuff pressure Pc goes up to around the average blood pressure Pb, a pulsating movement appears on the blood vessel wall which movement generates a volumetric pulse signal Sg on the volume signal Sv. Line (c) shows the waveforms of the volumetric pulse signal Sg. When the cuff pressure Pc reaches the value equal to the average blood pressure Pb, the amplitude of the volumetric pulse signal Sg becomes maximum. At this condition, the averaged value of the volume signal Sv and the value of the cuff pressure Pc are stored in a memory device of the control section 16, the former value being referred to as a servo target value Svs, the latter as a servo initial pressure Pcs. The actuation of the linear pump 6 is further continued in order to obtain the cuff pressure Pc larger than the blood pressure $\overline{Pb}$. Then, the volumetric pulse signal Sg gradually decreases and finally fades out to zero. When the cuff pressure Pc reaches a determined upper limit value such as 180 mm Hg, the control section 16 this time delivers logical "0" signals to the driver 21. As a result, the linear pump 6 is driven oppositely to thereby linearly decrease the cuff pressure Pc. At the time t1 shown in FIG. 2 when the cuff pressure Pc falls down to the servo target value Pcs, the linear pump 6 is stopped and the (a) terminal of the switch 20 is used for supplying the driver signal Se. The DC component of the driver signal Se is substantially zero at this condition, and has only the pulsating component of the volume signal Sv, that is, the volumetric signal Sg, so that the driver 21 is in a disabled state. The foregoing operation has been carried out in order to set the cuff pressure Pc at the servo target value Pcs and to obtain the average blood pressure $\overline{Pb}$.

Upon setting the cuff pressure Pc at the servo target value Pcs at the time t1, the gain control circuit 12 is supplied with a control signal C1. The gain control circuit 12 is adjusted to have such a gain as the volumetric pulse signal Sg can have a predetermined amplitude. This predetermined amplitude is illustratively shown at line (c) between the time t1 and t2. By setting such a gain, the amplitude difference of volumetric pulse signals between persons can be eliminated. The DC level deviation of the volume signal Sv from the servo target value Svs is detected in such a manner that a change of the predetermined amplitude of the volumetric pulse signal Sg is detected, and if the amount of change excesses a preset value, then the control section 16 controls the off-set voltage Vf to restore to its original servo target value Svs.

Then, at the time t2 as shown in FIG. 2, the control section 16 instructs to execute a next step where the shaker 7 is energized in accordance with the volumetric pulse signal Sg. In this operation, a feedback control is effected by controlling the variable Pc of the cuff pressure so that the volumetric pulse signal Sv is rendered zero, that is, the volume of the blood vessel is made constant. More in detail, the gain control circuit 18 is supplied with a control signal C2 in order that the amplitude of the drive signal Se is adjustably controlled to make the volumetric pulse signal Sg smaller by energizing the shaker 7 through the driver 19. In addition to the above, the phase of the volumetric pulse signal Sg is shifted by the phase compensator 14. Thus, the variable ΔPc of the cuff pressure generated by the shaker 7 is cancelled out by the blood pressure, and at the time t3 when the signal Sg becomes zero, the cuff pressure Pc equals to the blood pressure Pb. The blood pressure or intravascular pressure Pb can be obtained continuously and instantaneously from the amplifier 24 as a cuff pressure signal Sp which is displayed on the display section 27 in real time under a suitable blood scale.

It is to be noted here that after the time t2, the off-set voltage Vf and the gain of the gain control circuit 12 are maintained constant. In the case when the average blood pressure Pb changes after the time t2 and a DC component is superimposed upon the volumetric pulse signal Sg, the DC component is supplied through the phase compensator 14 and the gain control circuit 18 to the driver 21 to drive the linear pump 6. Accordingly, the average cuff pressure $\overline{Pc}$ restores to the average blood pressure $\overline{Pb}$.

It may be possible to display a cardiogram on the display section 27, or display other suitable physiological information.

What is claimed is:

1. In an automatic, continuous and indirect blood pressure measurement apparatus comprising:
   (a) a cuff which is adapted to be attached to a segment to be measured;
   (b) external force applying means for applying an external force to fluid contained in said cuff to thereby generate a cuff pressure;
   (c) a pressure sensor means for measuring said cuff pressure; and
   (d) a volume sensor means for detecting a volume per unit length of an artery of said segment, said volume varying in accordance with said cuff pressure and a pulsating intravascular pressure, said volume sensor means generating a volume signal corresponding to said volume, said volume signal comprising a DC component and a volumetric pulse signal, wherein said external force applying means is energized in accordance with said volumetric pulse signal shifted in phase and controlled in amplitude in order to control and maintain said volume per unit length constant and to obtain an instantaneous blood pressure of said artery as a function of said cuff pressure;

the improvement which comprises:

DC level adjustment and first gain control means which is supplied with an output from said volume sensor means, said output being subjected to DC level adjustment and amplitude control, said DC level adjustment and first gain control means generating a DC level adjusted and amplitude controlled volume signal;

phase compensator and second gain control means which controls the phase and amplitude of said volume signal from said DC level adjustment and first gain control means to generate said phase shifted and amplitude controlled volumetric pulse signal; and driver means responsive to said volumetric pulse signal shifted in phase and controlled in amplitude for driving said external force applying means.

2. The apparatus as claimed in claim 1, wherein said driver means comprises two drivers, one being aimed at amplifying a signal having a large DC variation and the other being aimed at amplifying a signal having a small DC variation, and wherein said external force applying means comprises two pressure applying devices, one being a linear pump and responsive to said one driver and the other being a shaker and responsive to the said other driver.

* * * * *